(12) United States Patent
Hsiao et al.

(10) Patent No.: US 6,346,269 B1
(45) Date of Patent: Feb. 12, 2002

(54) METHOD FOR PREPARING AN ORAL FORMULATION CONTAINING ACID-SENSITIVE DRUGS AND ORAL FORMULATION MADE THEREBY

(75) Inventors: Fang-Hsiung Hsiao; Chien-Chu Lin, both of Tainan Hsien; Ya-Ching Changchien, Kaohsiung, all of (TW)

(73) Assignee: Standard Chem. & Pharm. Co., Ltd., Tainan (TW)

( * ) Notice: Subject to any disclaimer, the term of this patent is extended or adjusted under 35 U.S.C. 154(b) by 0 days.

(21) Appl. No.: 09/567,083

(22) Filed: May 8, 2000

(51) Int. Cl.$^7$ .............. A61K 9/24; A61K 9/20; A61K 9/48; A61K 9/54

(52) U.S. Cl. .............. 424/472; 424/464; 424/465; 424/451; 424/458

(58) Field of Search .............. 424/464, 465, 424/458, 451, 472

(56) References Cited

U.S. PATENT DOCUMENTS 5,385,739 A * 1/1995 Debregeas et al. ......... 424/494
5,540,945 A * 7/1996 Ikushima ............... 424/490

* cited by examiner

Primary Examiner—Thurman K. Page
Assistant Examiner—Rachel M. Bennett
(74) Attorney, Agent, or Firm—Rosenberg, Klein & Lee

(57) ABSTRACT

The present invention relates to a method for preparing an oral formulation containing acid-sensitive drugs, including at least the following step: spreading a solution or a suspension containing at least stabilizers, solvents and acid-sensitive drugs or its pharmaceutically acceptable salts onto a core made from one or more excipients, and then drying the core to make an active ingredient layer over the core. Also disclosed is the oral formulation made by this method.

28 Claims, 4 Drawing Sheets

METHOD FOR PREPARING AN ORAL FORMULATION CONTAINING ACID-SENSITIVE DRUGS AND ORAL FORMULATION MADE THEREBY

BACKGROUND OF THE INVENTION

1. Field of the Invention

The present invention relates to a method for preparing an oral formulation containing acid-sensitive drugs, and especially to a method for preparing an oral formulation containing omeprazole having an layer of evenly distributed omeprazole coated on the core.

2. Description of Related Art

The acid-sensitive drugs essentially comprise substituted benzimidazole gastric anti-secretary agent such as omeprazole, lansoprazole, pantoprazole and pharmaceutically acceptable salts thereof. These agents are well-known strong inhibitors for inhibiting gastric acid secretion in mammals. The acid-sensitive drugs have irreversible inhibiting-action against the enzymatic system of H/K ATPase in the human body. In other words, they can inhibit the proton pumps of the gastroparietal cells. However, it is easy for the acid-sensitive drugs to decay in an acidic environment to become non-active ingredients. Therefore, there is a need in the field of the active ingredient manufacturing to overcome the above-mentioned problem.

For example, omeprazole is very unstable in an acidic environment. The half-life of degradation of omeprazole in water solutions at pH-values less than four is shorter than ten minutes. Even at neutral pH-values degradation proceeds rapidly, e.g. at pH=7 the half-life of omeprazole is about 14 hours. Therefore, omeprazole cannot exist in an acidic environment. The stability of omeprazole is also affected by moisture, heat, and organic solvents and to some degree by light. It is reported in some literature that omeprazole possesses acceptable stability in a base environment.

Owing to the stability of omeprazole, omeprazole should not contact gastric acid solution after administering the total formulation containing omeprazole, since the gastric acid solution will lower the activity of the omeprazole. Therefore, the oral formulation containing omeprazole is usually treated with an enteric coating to prevent the omeprazole from direct contact with the gastric acid solution. However, the enteric coating is usually made with acidic chemicals, thus when the oral formulation containing omeprazole is directly treated with the enteric coating, the omeprazole will rapidly decompose due to direct or indirect contact with the acidic ingredient in the enteric coating, such that the oral formulation will be discolored and the activity will be reduced during storage.

One conventional method for preparing an oral formulation containing omeprazole is proposed to overcome the above-mentioned problem. This conventional method consists of stabilizing the omeprazole by putting the omeprazole and a part of the excipients into an ammonia-containing environment instead of utilizing the base core consisting of omeprazole and base chemicals, and then spreading solutions onto the core with an eccentric separator while adding a globing agent from a supply funnel to form pellets containing the active ingredients.

However, the above-mentioned conventional method includes adding a globing agent at any time during preparing the pellets of the oral formulations. Such an addition of globing agent during the preparation of the pellets is very inconvenient in a process for preparing a pellet, and causes variable sizes of pellets resulting in a greater difference in terms of releasing rate of the oral formulation. Therefore, this conventional method is not acceptable to manufactures seeking a preparation method that is operated easily and can produce an homogeneously distributed oral preparation. In addition, the ammonia used in this conventional method also causes a problem of noxious fumes at the preparation site and is not environmentally friendly.

Therefore, there is still a need to provide a method for preparing an oral formulation with acid-sensitive drugs which solves the problem of the difference in pellet size and enhances the consistency of the releasing rate.

SUMMARY OF THE INVENTION

The objective of the present invention is to provide a method for preparing an oral formulation containing acid-sensitive drugs having a layer of evenly distributed active ingredient coated on the core.

To achieve the objective, the method in accordance with the present invention comprises:

(a) spreading a solution or a suspension comprising stablizers, solvents and acid-sensitive drugs or its pharmaceutically acceptable salts onto a core made from one or more excipients, and then drying the spread core to make a core with an active ingredient layer;

(b) spreading a solution or suspension comprising adhesives, plasticizer, anti-tackiness and solvents on the active ingredient layer containing the core achieved in (a) and then drying the solution or suspension to form a sub-coating layer over the active ingredient layer; and (c) spreading a suspension comprising enteric-soluble coating material, plasticizer, anti-tackiness agent and solvents onto the sub-coating layer achieved in (b) and then drying the spread suspension to make an enteric coating layer over the sub-coating layer. With the method in accordance with the present invention, the oral formulation containing acid-sensitive drugs has a layer of evenly distributed active ingredient layer coated on the core without active ingredients.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
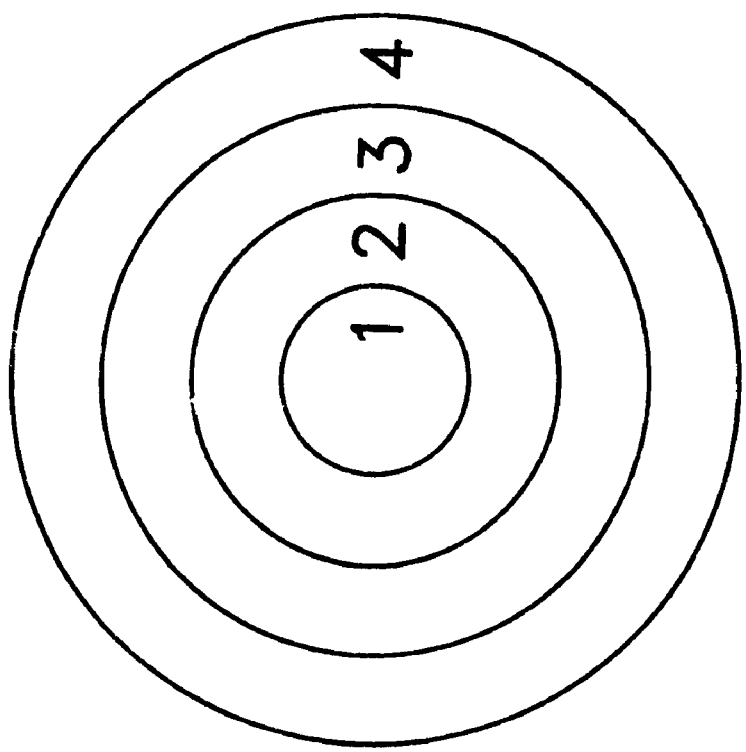
FIG. 1 is a cross-sectional plan view of one embodiment of the oral formulation containing acid-sensitive drugs in accordance with the present invention.

With reference to FIG. 1, the method in accordance with the present invention provides the oral formulation containing acid-sensitive drugs in the shape of a pellet that is circular in cross section and contains, from inside to outside, a core (1), an active ingredient-containing layer (2), a sub-coating layer (3) and an enteric coating layer (4). In addition, one or more active ingredient containing-layers (2) containing active ingredient and/or one or more sub-coating layers (3) can be applied between the core (1) and the enteric coating layer (4).

Although the preferred oral formulation is circular in cross-section, other suitable shape such as a granule, a tablet, a mini-tablet (the term "mini" means a size of from 3 mm to 5 mm) can be employed in the present invention.

Optionally, more than one layer (2) containing active ingredient and/or sub-coating layer (3) can be formed between the core (1) and the enteric coating layer (4). The prepared oral formulation can further be, either alone or together with other excipients, made into a active ingredient having a pharmaceutical amount of the oral formulation containing acid-sensitive drugs. For example it can be filled into a capsule or compressed into a tablet or a pellet.

The pellet shown in FIG. 1 is produced by the method in accordance with the present invention comprising the following steps:

(a) spreading a solution or a suspension comprising stablizers, solvents and acid-sensitive drugs or its pharmaceutically acceptable salts onto a core made from one or more excipients, and then drying the spread core to make a core coated with an active ingredient layer;

(b) spreading a composition solution or suspension comprising adhesives, plasticizer, anti-tackiness and solvents on the active ingredient layer containing the core achieved in (a) and then drying the solution or suspension to form a sub-coating layer over the active ingredient layer; and (c) spreading a suspension comprising enteric-soluble coating material and solvents onto the sub-coating layer achieved in (b) and then drying it to make an enteric coating layer over the sub-coating layer.

Details for each step will be described in the following.

In step (a), the core (1) can be prepared in advance or can be prepared in situ after forming the solution or suspension containing the acid-sensitive drugs or its pharmaceutically acceptable salts and the solvents with the stablizers. Therefore in one embodiment of the method in accordance with the present invention, the method is started by preparing a solution or a suspension by mixing the stablizers with the solvents.

The suitable solvents useful for the solution or suspension in the method in accordance with the present invention can be one member selected from the group consisting of water, alcohols, acetone, isopropanol, dichloromethane and compositions thereof. The preferable solvent includes ethanol, acetone and isopropanol.

The suitable stablizers useful for the solution or suspension in step (a) of the method in accordance with the present invention can be a member selected from the group consisting of hydroxides of alkali-metals and alkaline earth metals, bases of phosphates and organic acid salts and organic amines.

Subsequently, anti-tackiness and acid-sensitive drugs or its pharmaceutically acceptable salts are added to the solution or suspension to prepare a solution or suspension containing the active ingredient. Optionally, other agents such as adhesives, plasticizers or other diluents can be further added to the solution or suspension. Suitable anti-tackiness are selected from the group consisting of talc, stearic acid, stearate, sodium stearyl fumarate, glyceryl behenate, kaolin and aerosil.

Afterwards, one or more excipients such as microcrystalline cellulose or other pharmaceutically acceptable excipients are made into a core (1) in the shape of a pellet (as shown in FIG. 1) by a wet-granulation method. The apparatus for making the core (1) is, for example, a fluidized bed. In step (a), the pellet shaped-core preferably has a size of from 3 mm to 5 mm. In the case of a tablet or a mini-tablet, the core (1) can be formed by the direct tabletization method such as by a tablet making machine; and the tablet or mini-tablet made thereby also preferably has a size of from 3 mm to 5 mm.

Preferably, the core (1) used in the present invention is made from at least one of the excipients without any pharmaceutical activity. The excipient useful for the core (1) can be one of the members selected from the group consisting of lactose, starches, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin and castor oil.

Afterwards, the above-mentioned solution or suspension is spread onto the core (1). After drying it, layer (2) containing an active ingredient is formed over the core (1). The spreading of the solution or the suspension is completed by, for example, an atomizer.

In addition, the core (1) can be directly produced by a supplier. Readily available cores comprise: (a1) a granule core of sucrose; (a2) a granule core of sucrose and starch; and (a3) a granule core of micro-crystalline cellulose. In this case, step (a) may be adjusted to be supplying a core (1) and then spreading the active ingredient containing solution or suspension on the core (1).

Optionally, one or more adhesives can be added to prepare the core, which are selected from the group consisting of polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit®, copolymer of methyl acrylic acid/methyl methacrylate with polyvinyl acetate phthalate (PVAP).

Optionally, one or more plasticizers can be further added to prepare the core. Suitable plasticizers are selected from the group consisting of glycerin, polyethylene glycol, triethyl citrate, tributyl citrate, propanyl triacetate and castor oil.

Optionally, one or more diluents can further be added to prepare the core. Suitable diluents are selected from the group consisting of lactose, starch, mannitol, sodium carboxymethyl cellulose, sodium starch glycolate, sodium chloride, potassium chloride, pigments, salts of alginic acid, talc, titanium dioxide, stearic acid, stearate, microcrystalline cellulose, glycerin, polyethylene glycol, triethyl citrate, tributyl citrate, propanyl triacetate, dibasic calcium phosphate, tribasic sodium phosphate, calcium sulfate, cyclodextrin and castor oil.

After step (a), the layer (2) containing the active ingredient can contains 0.25 to 15% (w/w) of stablizers, 0.5% to 30% (w/w) of anti-tackiness, 0 to 25% (w/w) of plasticizers, 0 to 50% (w/w) of adhesives and the balance of acid-sensitive drugs or pharmaceutically acceptable salts thereof.

In step (b), the sub-coating layer (3) is coated on the active ingredient layer (2) by spreading the solution or suspension comprising adhesives, plasticizers, anti-tackiness and solvents onto the active ingredient layer (2) containing the core (1) prepared in step (a) and then drying it. The solution or the suspension is spread by being atomized by a nozzle. The nozzle used in the present invention is also well-known to those skilled in the art, thus it is not discussed in detail.

Optionally, plasticizers or other diluents can be added in the solution or suspension prepared by step (b).

The adhesives suitably used in step (b) can be the same one as used in step (a) and also can be a member of the group consisting of polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalate acid (CAP) xanthan gum, alginic acid, salts of alginic acid, Eudragit, and a copolymer of methyl acrylic acid/methyl methacrylate with polyvinyl acetate phthalate (PVAP).

The plasticizer useful in step (b) is selected from the group consisting of glycerin, polyvinyl alcohol, triethyl citrate, tributyl citrate, propanyl triacetate and castor oil.

The anti-tackiness useful in step (b) is selected from the group consisting of talc, stearic acid, stearate, sodium stearyl fumarate, glyceryl behenate, kaolin, and aerosil.

The solvents useful in step (b) can be the same as those used in step (a) and can be selected from the group consisting of water, alcohols, acetone, isopropanol, dichloromethane and compositions thereof.

The diluents useful in step (b) can be the same as those used in step (a) and can be selected from the group consisting of lactose, starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin and castor oil.

In step (c), the suspension containing enteric-soluble coating material and solvents is also spread onto the sub-coating layer (3) by atomization by using a nozzle. After drying it, an enteric coating layer (4) is formed over the sub-coating layer (3).

The enteric-soluble coating material suitable for the present invention is selected from the group consisting of hydroxypropyl methylcellulose acetate succinate (HPMCAS), hydroxypropyl methyl cellulose phthalate (HPMCP), cellulose of acetate phthalate(CAP), polyvinyl phthalic acetate (PVPA), Eudragit and shellac.

Optionally, plasticizers and anti-tackiness can further be added to the enteric coating layer. The solvents, plasticizers and anti-tackiness useful in step (c) and be the same as those used in step (a).

The plasticizer useful in step (c) is selected from the group consisting of glycerin, polyethylene glycol, triethyl citrate, tributyl citrate, propanyl triacetate and castor oil.

The anti-adhesive useful in step (c) is selected from the group consisting of talc, stearic acid, stearate, sodium stearyl fumarate, glyceryl behenate, kaolin and aerosil.

The solvents useful in step (c) can be the same as those used in step (a) and can be selected from the group consisting of water, alcohols, acetone, isopropanol, dichloromethane and compositions thereof.

EXAMPLES

Following examples are provided to further explain the present invention. However, the scope of the present invention should not be limited by these examples.

Example 1

| | Formulation: | |
|---|---|---|
| (1) | core | 450 g |
| (2) | layer containing the active ingredient: | |
| | omeprazole | 80 g |
| | HPC | 16 g |
| | Polyethylene glycol (PEG 6000) | 10 g |
| | Dibasic sodium phosphate ($Na_2HPO_4$) | 1.4 g |
| | Tribasic sodium phosphate ($Na_3PO_4$) | 1.4 g |
| | Talc | 24 g |
| | Pure water | 800 ml |
| (3) | sub-coating layer: | |
| | HPC | 32 g |
| | PEG 6000 | 16 g |
| | Talc | 32 g |
| | Pure water | 600 ml |
| (4) | enteric coating layer: | |
| | HPMCAS | 110.4 g |
| | Triethyl citrate | 30.8 g |
| | Talc | 34.8 g |
| | Pure water | 1,100 ml |

Procedure:

10 g of PEG 6000, 16 g of HPC and 800 ml of pure water were mixed together to prepare an aqueous solution.

Then, 1.4 g of dibasic sodium phosphate and 1.4 g of tribasic sodium phosphate were poured and mixed into the prepared aqueous solution.

Subsequently, 80 g of omeprazole and 24 g of talc were poured into the prepared solution to make a suspension containing an active ingredient. The suspension containing the active ingredient was spread, in an atomized manner, onto the cores in a fluidized bed to make an active ingredient layer containing the pellets after drying.

Afterward, a suspension was prepared by mixing 32 g of HPC, 16 g of polyethylene glycol(PEG), 32 g of talc and 600 ml of pure water. The prepared suspension was then spread on the active ingredient layer containing the pellets in atomized manner to make a sub-coating layer over the active ingredient layer after drying.

Finally, a suspension was prepared by mixing 110.4 g of HPMCAS, 30.8 g of triethyl citrate, 34.8 g of talc and 1,100 ml of pure water and then the prepared suspension was spread on the pellets over the sub-coating layer to serve as the enteric coating layer after drying.

Example 2

| | Formulation: | |
|---|---|---|
| (1) | core: | 450 g |
| (2) | active ingredient layer: | |
| | omeprazole | 80 g |
| | HPMC | 12 g |
| | Polyethylene glycol (PEG 4000) | 8 g |
| | $Na_2HPO_4$ | 7.5 g |
| | Talc | 24 g |
| | Pure water | 800 ml |
| (3) | sub-coating layer | |
| | HPMC | 32 g |
| | PEG 4000 | 16 g |
| | $Na_3PO_4$ | 2.4 g |

-continued

| Formulation: | | |
|---|---|---|
| | Talc | 32 g |
| | Pure water | 600 ml |
| (4) | enteric coating layer: | |
| | HPMCAS | 110.4 g |
| | Triethyl citrate | 30g |
| | Talc | 35g |
| | Pure water | 1,100 ml |

Procedure:

8 g of Polyethylene glycol, 12 g of HPMC and 800 ml of pure water were mixed together to prepare an aqueous solution.

Then, 7.5 g of dibasic sodium phosphate was added to the prepared solution.

Subsequently, 80 g of omeprazole and 24 g of talc were added to the prepared solution to prepare a suspension. Then, the suspension was spread on cores in a fluidized bed to prepare an active ingredient layer containing the pellets after drying.

Afterward, 32 g of HPMC, 16 g of polyethylene glycol, 2.4 g of tribasic sodium phosphate, 32 g of talc and 600 ml of pure water were mixed to prepare a suspension composition. The suspension composition was then spread on the active ingredient layer containing the pellets and dried to form sub-coating layers over the active ingredient layers.

Finally, 110.4 g of HPMCAS, 30 g of triethyl citrate, 35 g of talc and 1,100 ml of pure water were mixed together to prepare a suspension composition. The composition was spread on the pellets over the sub-coating layers and was dried to become the enteric coating layer.

Example 3

| (1) | core: | 420 g | |
|---|---|---|---|
| (2) | active ingredient layer: | | |
| | omeprazole | 60 | g |
| | polyvinyl pyrrolidone (PVP k30) | 12 | g |
| | polyethylene glycol (PEG6000) | 8 | g |
| | Na$_3$PO$_4$ | 6.5 | g |
| | Talc | 24 | g |
| | Pure water | 600 | ml |
| (3) | sub-coating layer: | | |
| | HPMC | 24 | g |
| | PEG 6000 | 12 | g |
| | Na$_3$PO$_4$ | 2.4 | g |
| | Talc | 24 | g |
| | Pure water | 450 | ml |
| (4) | enteric coating layer: | | |
| | HPMCAS | 90 | g |
| | Triethyl citrate | 20 | g |
| | Talc | 28 | g |
| | Pure water | 900 | ml |

Procedure:

8 g of polyethylene glycol, 12 g of PVP k30 and 600 ml of pure water were mixed to prepare an aqueous solution.

Then 6.5 g of tribasic sodium phosphate was poured in the prepared solution.

Subsequently, 60 g of omeprazole and 24 g of talc were poured into the prepared solution to prepare a suspension containing an active ingredient. Then, the suspension was spread on the cores in a fluidized bed and was dried to make an active ingredient layer containing the cores.

Afterward, a solution of 24 g of HPMC, 12 g of polyethylene glycol, 2.4 g of tribasic sodium phosphate, 24 g of talc and 450 ml of pure water were spread on the active ingredient layer containing the cores and was dried to form the sub-coating layer over the active ingredient layer.

Finally, 90 g of HPMCAS, 20 g of triethyl citrate, 28 g of talc and 900 ml of pure water were mixed together to prepare a suspension composition, and then the suspension composition was spread onto the sub-coating layer of each core and dried to form an enteric coating layer on each core.

Example 4

The pellets prepared according to Example. 1 were filled in capsules made of gelatin.

Example 5

The pellets prepared according to Example. 2 were filled in capsules made of gelatin.

Example 6

(control)

Market-available omeprazole oral formulation.

Dissolution test:

Pellets acquired according to Example. 4, 5 and 6 were tested. The releasing test was carried out according to "Releasing Test, The United States Pharmacopoeia, version 24" in terms of the pH-change.

Figure 2:
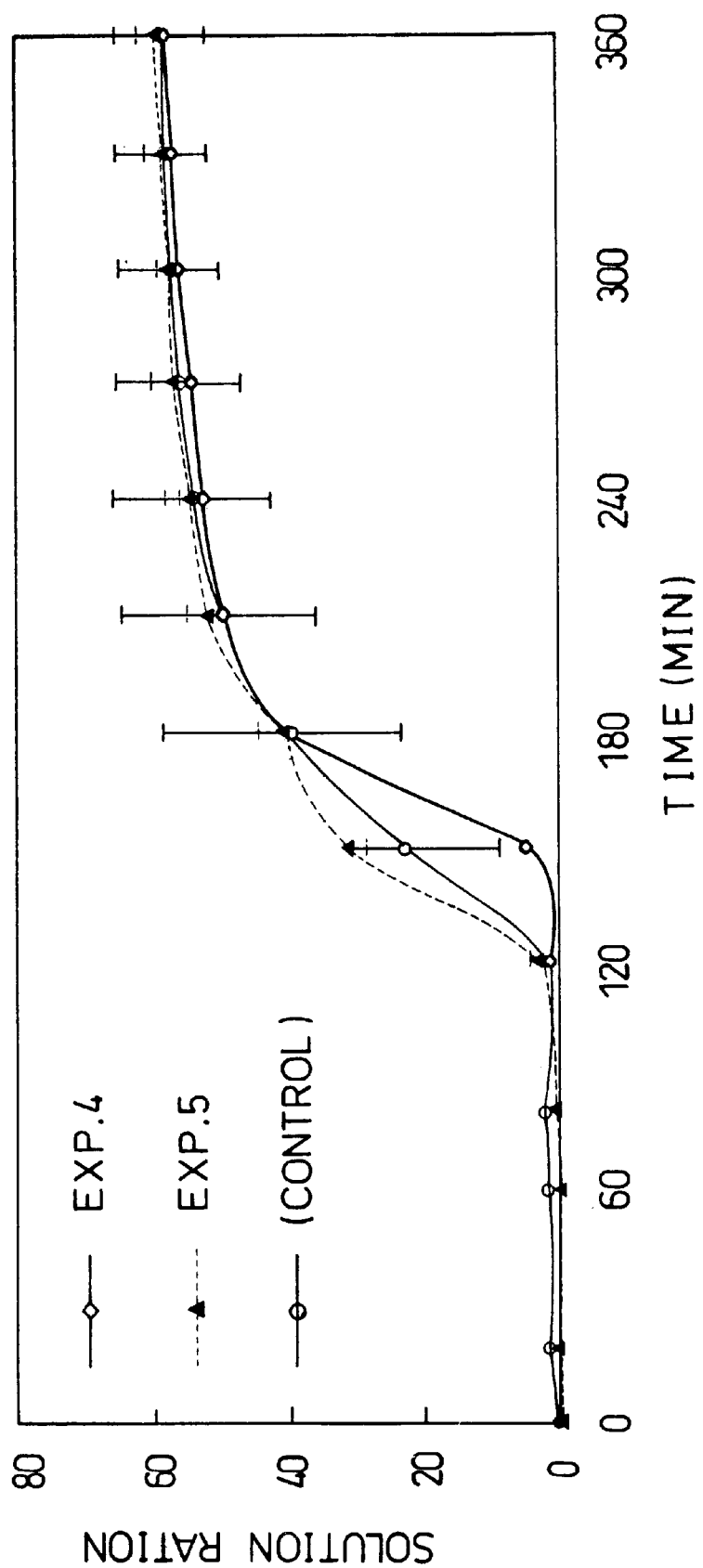
FIG. 2 is a graph showing the active ingredient-dissolution rates of the oral formulations each containing acid-sensitive drugs made by the present invention and prior art.

750 ml of 0.1N aqueous solution of hydrochloride was poured into a tank and then heated to a temperature of 37±0.5° C. The rotation velocity of the paddle was adjusted to be 50 rpm. After two hours, 250 ml of 0.2N aqueous solution of tribasic sodium phosphate was added to the tank. The releasing rate was measured and the graph of the releasing ratio VS time was acquired. The results are listed in table 1 and presented graphically in FIG. 2.

Table 1 (the releasing ratio (%) of the tested pellets in pH-change releasing solution)

| | Example. 4 | | Example. 5 | | Example. 6 | |
|---|---|---|---|---|---|---|
| Time | Ave. | | Ave. | | (control) | |
| (min) | (%) | St. Error | (%) | St. Error | Ave. (%) | St. Error |
| 0 | 0.00 | 0.00 | 0.00 | 0.00 | 0.00 | 0.00 |
| 20 | 0.04 | 0.10 | 0.40 | 0.04 | 1.14 | 0.22 |
| 60 | 0.50 | 0.20 | 0.14 | 0.05 | 1.39 | 0.29 |
| 80 | 0.45 | 0.21 | 0.83 | 0.22 | 1.46 | 0.33 |
| 120 | 0.89 | 0.21 | 3.39 | 0.62 | 1.54 | 0.41 |
| 150 | 4.50 | 0.54 | 31.10 | 3.01 | 22.30 | 13.94 |
| 180 | 39.50 | 2.10 | 41.20 | 3.09 | 40.56 | 17.77 |
| 210 | 49.40 | 2.15 | 52.23 | 3.05 | 50.19 | 14.38 |
| 240 | 52.60 | 3.21 | 55.25 | 3.15 | 54.22 | 11.75 |
| 270 | 54.36 | 2.41 | 57.52 | 3.15 | 56.22 | 9.33 |
| 300 | 56.54 | 2.15 | 58.21 | 1.59 | 57.67 | 7.58 |
| 330 | 57.21 | 2.20 | 59.21 | 2.15 | 58.61 | 6.79 |
| 360 | 58.41 | 0.54 | 60.25 | 2.20 | 58.94 | 6.65 |

From table 1, it was determined that the average dissolution rate in each of Example. 4, Example. 5 and Example. 6 was lower than 10%, which meets the requirements that the enteric coating layer is not allowed to be released in 0.1N aqueous solution of hydrochloride. However, the standard error in each of Example. 4 and Example. 5 is much less than that of Example. 6 that is interpreted to mean that the consistency in the dissolution rate of each of Example. 4 and Example. 5 is superior to that of Example. 6.

Example 7

Formulation:

| | | | |
|---|---|---|---|
| (1) | core: | | |
| | starch | 180 | g |
| | micro-crystalline cellulose | 220 | g |
| | CaHPO$_4$ | 60 | g |
| | Magnesium stearate | 5 | g |
| (2) | active ingredient layer: | | |
| | omeprazole | 60 | g |
| | polyvinyl pyrrolidone (PVP k30) | 12 | g |
| | polyethylene glycol (PEG 6000) | 8 | g |
| | tribasic sodium phosphate | 6.5 | g |
| | talc | 24 | g |
| | pure water | 600 | ml |
| (3) | sub-coating layer | | |
| | HPMC | 100 | g |
| | Polyethylene glycol | 12 | g |
| | Na$_3$PO$_4$ | 2.4 | g |
| | Talc | 24 | g |
| | Pure water | 450 | ml |
| (4) | enteric coating layer: | | |
| | copolymer of methacrylic acid/ methacrylate (Eudragit L30D) | 24 | g |
| | triethyl citrate | 20 | g |
| | talc | 48 | g |
| | pure water | 500 | ml |

Procedure:

180 g of starch, 220 g of micro-crystalline cellulose, 60 g of CaHPO$_4$ and 5 g of magnesium stearate were evenly mixed together and then the mixture was pressed by a tablet-making machine into minitablets having a diameter of 3 mm to serve as cores.

8 g of polyethylene glycol, 12 g of polyvinyl pyrrolidone and 600 ml of pure water were mixed to prepare an aqueous solution. Then, 6.5 g of Na$_3$PO$_4$ was poured into the prepared aqueous solution.

Subsequently, 60 g of omeprazole and 24 g of talc were added to the prepared solution to prepare a suspension containing an active ingredient. The suspension containing the active ingredient was then spread onto the cores in a fluidized bed and was then dried to prepare the pellets containing the active ingredient.

Afterward, 24 g of HPMC, 12 g of polyethylene glycol, 2.4 g of Na$_3$PO$_4$ 24 g of talc and 450 ml of pure water were mixed to prepare a suspension composition, and the composition was spread on the pellets containing the active ingredient to serve as a sub-coating layer after drying.

Finally, 100 g of copolymer of methacrylic acid/ methacrylate, 20 g of triethyl citrate, 48 g of talc and 500 ml of pure water were mixed to prepare a suspension composition, and the suspension composition was spread on the sub-coating layer of each core to serve as an enteric coating layer after drying.

Example 8

Formulation:

| | | | |
|---|---|---|---|
| (1) | core: | | |
| | anhydrous lactose | 90 | g |
| | starch | 220 | g |
| | micro-crystalline cellulose | 180 | g |
| | CaHPO$_4$ | 50 | g |
| | pure water | 100 | ml |
| | magnesium stearate | 5 | g |
| (2) | active ingredient layer: | | |
| | omeprazole | 80 | g |
| | polyvinyl pyrrolidone (PVP K30) | 12 | g |
| | polyethylene glycol (PEG 6000) | 8 | g |
| | Na$_3$PO$_4$ | 4.5 | g |
| | Talc | 24 | g |
| | Pure water | 600 | ml |
| (3) | sub-coating layer: | | |
| | HPMC | 24 | g |
| | Polyethylene glycol (PEG6000) | 12 | g |
| | Na$_3$PO$_4$ | 2.4 | g |
| | Talc | 24 | g |
| | Pure water | 450 | ml |
| (4) | enteric coating layer: | | |
| | copolymer of methacrylic acid/ methacrylate (Eudragit L30D) | 100 | g |
| | triethyl citrate | 20 | g |
| | talc | 48 | g |
| | pure water | 500 | ml |

Procedure:

90 g of anhydro-lactose, 220 g of starch, 180 g of micro-crystalline cellulose and 50 g of CaHPO$_4$ were added to 100 ml of pure water and evenly mixed with 5 g of magnesium stearate, and then the mixture was made into tablets in a tablet-making machine.

8 g of polyethylene glycol and 12 g of polyvinyl pyrrolidone were added to 600 ml of pure water to prepare an aqueous solution. Then, 4.5 g of Na$_3$PO$_4$ was added to the prepared solution.

Subsequently, 80 g of omeprazole and 24 g of talc were added into the prepared solution to prepare a suspension containing an active ingredient, and the suspension was spread on the tablets in a fluidized bed to prepare pellets containing the active ingredient-after drying.

Afterward, 24 g of HPMC, 12 g of polyethylene glycol, 2.4 g of Na$_3$PO$_4$, 24 g of talc and 450 ml of pure water were mixed to prepare a suspension composition, and the composition was spread on the pellet cores to form a sub-coating layer after drying.

Finally, 100 g of copolymer of methacrylic acid/ methacrylate, 20 g of triethyl citrate, 48 g of talc and 500 ml of pure water were mixed to prepare a suspension composition, and the suspension composition was spread on each core over the sub-coating layer to form an enteric coating layer on each core after drying.

Example 9

Formulation:

| | | | |
|---|---|---|---|
| (1) | core: | 450 | g |
| (2) | active ingredient layer: | | |
| | lansoprazole | 80 | g |
| | HPMC | 12 | g |
| | Polyethylene glycol (PEG 6000) | 8 | g |
| | Na$_3$Po$_4$ | 6.5 | g |
| | Talc | 24 | g |
| | Pure water | 600 | ml |

-continued

| | Formulation: | |
|---|---|---|
| (3) | sub-coating layer: | |
| | HPMC | 24 g |
| | Polyethylene glycol (PEG6000) | 12 g |
| | Na$_3$PO$_4$ | 2.4 g |
| | Talc | 24 g |
| | Pure water | 450 ml |
| (4) | enteric coating layer: | |
| | copolymer of methacrylic acid/ methacrylate (Eudragit L30D) | 60 g |
| | triethyl citrate | 20 g |
| | talc | 48 g |
| | pure water | 500 ml |

Procedure:

8 g of polyethylene glycol, 12 g of HPMC and 600 ml of pure water were mixed to prepare an aqueous solution, and then 6.5 g of tribasic sodium phosphate was added to the prepared solution.

80 g of lansoprazole and 24 g of talc were added to the prepared solution to prepare a suspension containing an active ingredient, and the suspension containing the active ingredient was spread on cores in a fluidized bed to prepare pellets coated with the active ingredient layer after drying.

Subsequently, 24 g of HPMC, 12 g of polyethylene glycol, 2.4 g of Na$_3$PO$_4$, 24 g of talc and 450 ml of pure water were mixed to prepare a suspension composition, and the composition was spread on the prepared pellets to form a sub-coating layer over each active ingredient layer after drying.

Finally, 60 g of HPMCAS, 20 g of triethyl citrate, 48 g of talc and 500 ml of pure water were mixed to prepare a suspension, and the suspension was spread on each core over the sub-coating layer to form an enteric coating layer after drying.

Example 10

| (1) | core: | |
|---|---|---|
| | anhydrous lactose | 40 g |
| | starch | 200 g |
| | micro-crystalline cellulose | 120 g |
| | CaHPO$_4$ | 80 g |
| | Pure water | 100 ml |
| (2) | active ingredient layer: | |
| | pentroprazole | 60 g |
| | HPMC | 19 g |
| | Polyethylene glycol (PEG 6000) | 9 g |
| | Na$_3$PO$_4$ | 6.5 g |
| | Talc | 24 g |
| | Pure water | 600 ml |
| (3) | sub-coating layer: | |
| | HPMC | 24 g |
| | polyethylene glycol (PEG 6000) | 12 g |
| | Na$_3$PO$_4$ | 2.4 g |
| | Talc | 24 g |
| | Pure water | 450 ml |
| (4) | enteric coating layer: | |
| | HPMCAS | 60 g |
| | Triethyl citrate | 20 g |
| | Talc | 48 g |
| | Pure water | 500 ml |

Procedure:

40 g of anhydro lactose, 200 g of starch, 120 g of micro-crystalline cellulose and 60 g of CaHPO$_4$ were added to 100 ml of pure water to prepare cores after pelletizing.

9 g of polyethylene glycol, 19 g of HPMC and 600 ml of pure water were mixed to prepare an aqueous solution. Then, 6.5 g of Na$_3$PO$_4$ was added to the aqueous solution.

Subsequently, 60 g of pentroprazole and 24 g of talc were added to the prepared solution to prepare a suspension containing an active ingredient, and the suspension was spread on the cores in a fluidized bed to prepare pellets coated with an active ingredient layer after drying.

Afterward, 24 g of HPMC, 12 g of polyethylene glycol, 2.4 g of Na$_3$PO$_4$, 24 g of talc and 450 ml of pure water were mixed to prepare a suspension, and the suspension was spread on each core over the active ingredient layer to form a sub-coating layer after drying.

Finally, 60 g of HPMCAS, 20 g of triethyl citrate, 48 g of talc and 500 ml of pure water were mixed to prepare a suspension composition, and the composition was spread on each core over the sub-coating layer to form an enteric coating layer.

Example 11

Figure 3:
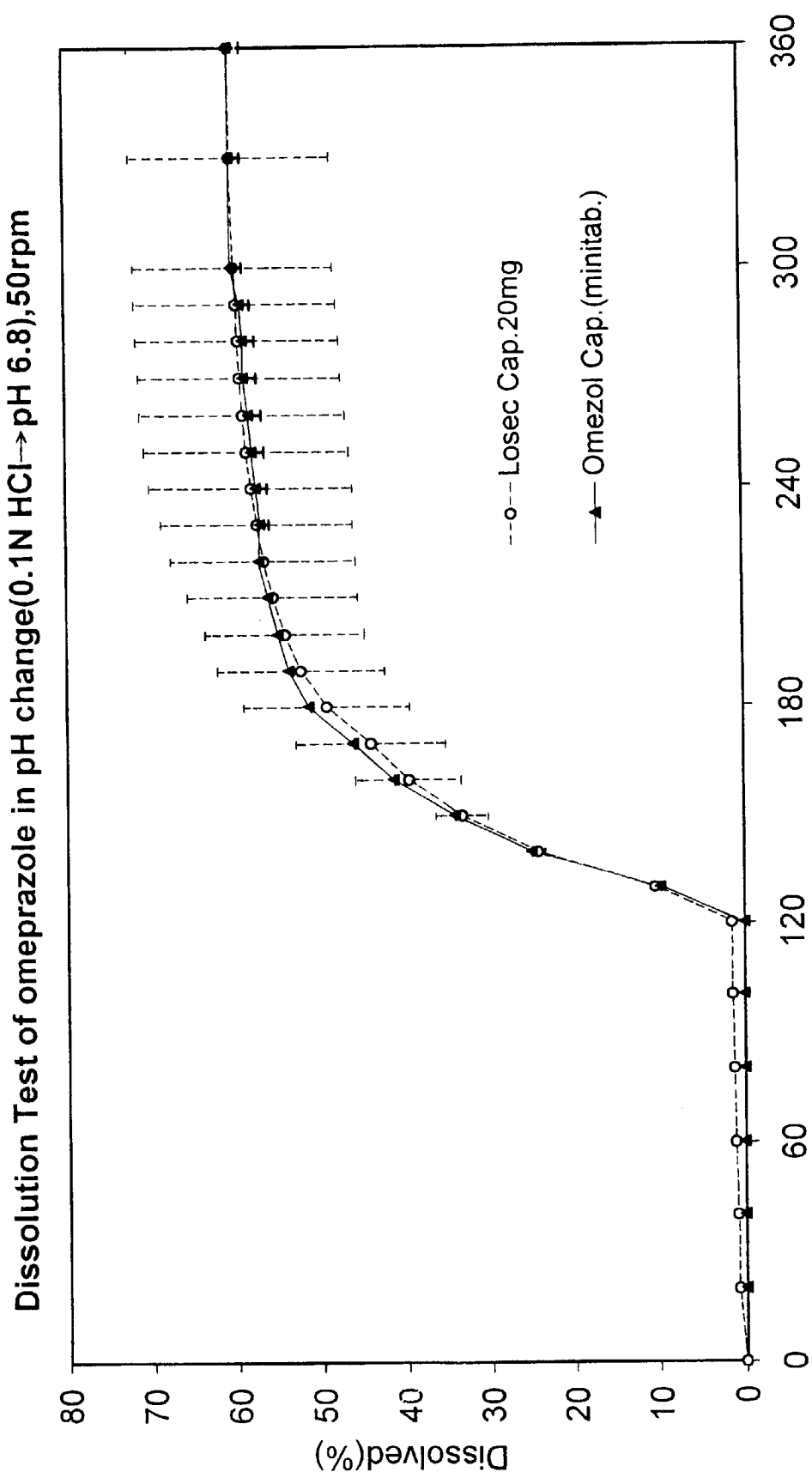
FIG. 3 is a graph showing the active ingredient-releasing rates of the oral formulations each containing acid-sensitive drugs made by the present invention and prior art.
Figure 4:
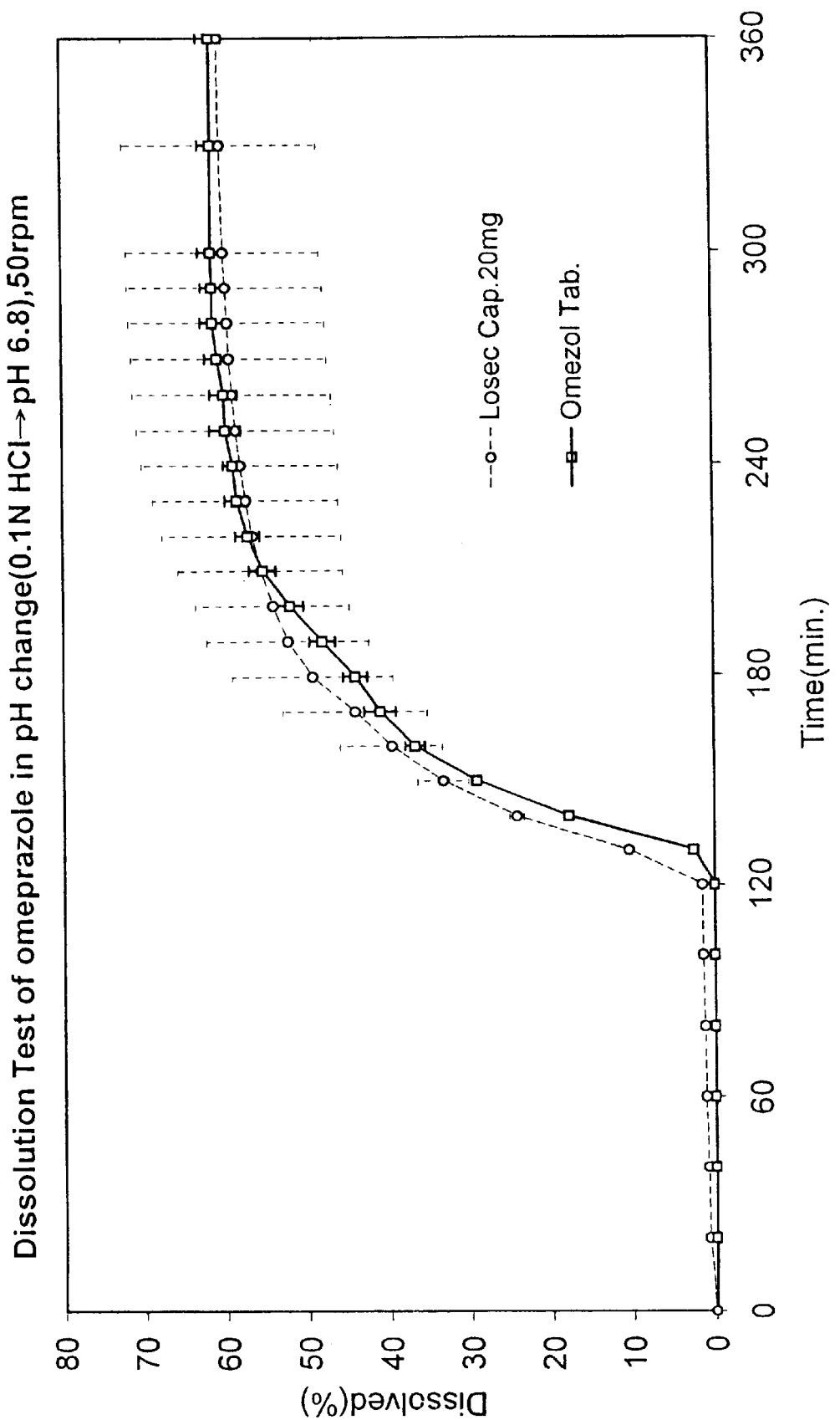
FIG. 4 is a graph showing the active ingredient-releasing rates of the oral formulations each containing acid-sensitive drugs made by the present invention and prior art.

The procedure of Example. 6 was repeated with the exception that the oral formulations to be tested were the mini-tablets made in Example. 7 and tablets made in Example. 8. The testing results are shown in FIGS. 3 and 4. As shown in FIGS. 3 and 4, both the mini-tablets made in Example. 7 and the tablets made in Example. 8 have a releasing ratio of under 10% at 120 min, which meets the requirements that the enteric products are not allowed to be resolved in 0.1N aqueous solution of hydrochloride.

Although the present invention has been explained relative to its preferred embodiment, it is to be understood that many other possible modifications and variations can be made without departing from the spirit and scope of the invention as hereinafter claimed.

What is claimed is:

1. A method for preparing an oral formulation containing acid-sensitive drugs comprising:
   (a) spreading a solution or a suspension consisting essentially of stabilizers, an inorganic solvent and acid-sensitive drugs or its pharmaceutically acceptable salts on a core made from one or more excipients, and then drying the spread core to make a core coated with an active ingredient layer;
   (b) spreading a composition solution or suspension consisting essentially of adhesives, plasticizer, anti-tackiness and an inorganic solvent on the active ingredient layer containing the core achieved in (a) and then drying it to form a sub-coating layer over the active ingredient layer; and
   (c) spreading a suspension comprising enteric-soluble coating material and an inorganic solvent on the sub-coating layer achieved in (b) and then drying it to make an enteric coating layer over the sub-coating layer.

2. The method as claimed in claim 1, wherein the acid-sensitive drugs is substituted benzimidazole gastric anti-secretary agent selected from the group consisting of omeprazole, lansoprazole, pentroprazole and pharmaceutically acceptable salts thereof.

3. The method as claimed in claim 1, wherein the core in step (a) is a pellet core made by a wet granulation method.

4. The method as claimed in claim 1, wherein the core in step (a) is a tablet made by a wet granulation method.

5. The method as claimed in claim 1, wherein the core in step (a) is a mini-tablet made by a wet granulation method.

6. The method as claimed in claim 1, wherein the core (1) is a pellet core.

7. The method as claimed in claim 1, wherein the core (1) is a tablet core made by tablet-making machine.

8. The method as claimed in claim 1, wherein the core (1) is a mini-tablet core made by tablet-making machine.

9. The method as claimed in claim 8, wherein the mini-tablet has a size of from 3 mm to 5 mm.

10. The method as claimed in claim 1, wherein one or more additives selected from the group consisting of adhesives, plasticizers and diluents are further added in step (a) to prepare the core.

11. The method as claimed in claim 1, wherein one or more additives selected from the group consisting of plasticizers and diluents are further added in the solvents of step (b).

12. The method as claimed in claim 1, wherein one or more additives selected from the group consisting of plasticizers and anti-tackiness are further added to the solvents of step (c).

13. The method as claimed in claim 1, wherein the inorganic solvent is water.

14. The method as claimed in claim 1, wherein the adhesives are selected from the group consisting of polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalate (CAP), copolymer of methyl acrylic acid/methyl methacrylate with polyvinyl acetate phthalate (PVAP).

15. The method as claimed in claim 10, wherein the plasticizers are selected from the group consisting of glycerin, polyethylene glycol, triethyl citrate, tributyl citrate, propanyl triacetate and castor oil.

16. The method as claimed in claim 11, wherein the plasticizers are selected from the group consisting of glycerin, polyethylene glycol, triethyl citrate, tributyl citrate, propanyl triacetate and castor oil.

17. The method as claimed in claim 12, wherein the plasticizers are selected from the group consisting of glycerin, polyethylene glycol, triethyl citrate, tributyl citrate, propanyl triacetate and castor oil.

18. The method as claimed in claim 10, wherein the one or more diluents are selected from the group consisting of lactose, starch, mannitol, glycolate sodium carboxymethyl cellulose, sodium starch, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin and castor oil.

19. The method as claimed in claim 11, wherein the one or more diluents are selected from the group consisting of lactose, starch, mannitol, sodium carboxymethyl cellulose, sodium starch, glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin and castor oil.

20. The method as claimed in claim 1, wherein the anti-tackiness are selected from the group consisting of talc, stearic acid, stearate, sodium stearyl fumarate, glyceryl behenate, kaolin and aerosil.

21. The method as claimed in claim 1, wherein the excipient is selected from the group consisting of lactose, starches, mannitol, sodium carboxymethyl cellulose, sodium starch, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic calcium phosphate, calcium sulfate, cyclodextrin and castor oil.

22. The method as claimed in claim 1, wherein the stablizers are selected from the group consisting of hydroxides of alkali-metals and alkaline earth metals, bases of phosphates and organic acid salts, and organic amines.

23. The method as claimed in claim 1, wherein the active ingredient layer contains 0.25 to 15%(w/w) of stablizers, 0.5% to 30% (w/w) of anti-tackiness, 0 to 25% (w/w) of plasticizers, 0 to 50% (w/w) of adhesives and the balance of omeprazole or pharmaceutically acceptable salts thereof.

24. The method as claimed in claim 1, wherein the oral formulation containing acid-sensitive drugs can be filled into a capsule alone to make a pharmacy containing dose-amount of the active ingredients.

25. The method as claimed in claim 1, wherein the oral formulation containing acid-sensitive drugs can be further mixed with other pharmaceutically acceptable excipients and tabletized into tablets.

26. The method as claimed in claim 3, wherein the pellets can further be compressed into a tablet.

27. The method as claimed in claim 3, wherein the pellets can further be compressed into a mini-tablet.

28. An oral formulation containing acid-sensitive drugs, comprising:

a core (1) made of one or more excipients, at least one active ingredient-containing layer (2) having an evenly distributed active ingredient consisting essentially of a stabilizer component, an inorganic solvent component, and an acid-sensitive drug component or its pharmaceutically acceptable salt, the active ingredient-containing layer (2) covering the core (1), at least one sub-coating layer (3) covering the layer (2) containing the active ingredient, the sub-coating layer (3) consisting essentially of adhesive, plasticizer and tackiness, and inorganic solvent components; and an enteric coating layer and an inorganic solvent (4) formed over the sub coating layer (3).

* * * * *